(12) United States Patent
Demrose et al.

(10) Patent No.: US 6,704,937 B2
(45) Date of Patent: Mar. 16, 2004

(54) THUMB SLEEVE FOR THUMB WRESTLING GAME

(76) Inventors: Richard S. Demrose, 5657 Highview, Dearborn Heights, MI (US) 48127; Sharon Demrose, 5657 Highview, Dearborn Heights, MI (US) 48127

( * ) Notice: Subject to any disclaimer, the term of this patent is extended or adjusted under 35 U.S.C. 154(b) by 286 days.

(21) Appl. No.: 09/970,119

(22) Filed: Oct. 3, 2001

(65) Prior Publication Data

US 2003/0065282 A1 Apr. 3, 2003

(51) Int. Cl.⁷ .......................... A63B 71/00; A41D 19/00
(52) U.S. Cl. ............................................... 2/21; 273/452
(58) Field of Search ............................... 2/21, 160, 455, 2/163; 223/101; 128/880; 273/452, 459; D2/610, 617; 602/5, 41, 62, 63

(56) References Cited

U.S. PATENT DOCUMENTS

| | | | | |
|---|---|---|---|---|
| 1,516,385 A | * | 11/1924 | Keck | 2/21 |
| 2,351,906 A | * | 6/1944 | Beatty | 2/21 |
| 2,925,605 A | * | 2/1960 | Wheeler | 2/21 |
| 3,728,736 A | * | 4/1973 | Pugh | 2/21 |
| 3,790,165 A | | 2/1974 | Schmidt et al. | |
| 4,178,589 A | | 12/1979 | Nunn et al. | |
| 4,733,410 A | * | 3/1988 | Glotkin | 2/21 |
| 4,953,568 A | | 9/1990 | Theisler | |
| 4,998,724 A | | 3/1991 | Hartman | |
| 5,010,901 A | | 4/1991 | Pales | |
| 5,497,510 A | | 3/1996 | Knowles et al. | |
| 5,682,611 A | | 11/1997 | Kline | |
| 5,899,870 A | | 5/1999 | Deirmendjian et al. | |

* cited by examiner

*Primary Examiner*—Tejash Patel
(74) *Attorney, Agent, or Firm*—Dale J. Ream

(57) ABSTRACT

A thumb sleeve for use in playing a thumb wrestling game includes a head member having a generally cylindrical configuration and constructed of a resilient material for fitting snuggly on the thumb of a player. The thumb sleeve includes a sheath having a generally cylindrical configuration connected to the head member. The sheath is constructed of an interwoven mesh material defining a diameter that increases when ends of the sheath are urged toward one another and decreases when ends of the sheath are urged away from one another. The sheath anchors and stabilizes the head member during vigorous game play and facilitates removal when relaxed.

12 Claims, 3 Drawing Sheets

THUMB SLEEVE FOR THUMB WRESTLING GAME

BACKGROUND OF THE INVENTION

The present invention relates generally to amusement devices and, more particularly, to a thumb sleeve for wear on a player's thumb when playing a thumb wrestling game.

The game of thumb wrestling is enjoyed by both children and adults, the game involving two players interlocking their fingers together in an inwardly curled configuration and then using their thumbs to outmaneuver and pin their opponent's thumb. Various devices have been proposed for enhancing game play with wrestling ring accessories or with stabilizing devices, such as the devices shown in U.S. Pat. Nos. 3,790,165 and 4,998,724. Although assumably effective for their intended purposes, the existing devices diminish the players' ability to interlock their fingers or to have free movement during vigorous game play.

Therefore, it is desirable to have a device for wear upon a player's thumb for use in thumb wrestling that does not encumber or distract a player's movement during game play. Further, it is desirable to have a device which will not become dislodged from a player's thumb during game play.

SUMMARY OF THE INVENTION

A thumb sleeve according to the present invention for wear upon a player's thumb while playing the game of thumb wrestling includes a head member connected to an anchor sheath. The head member is in the form of a thumb puppet and includes a hollow cylindrical configuration of a resilient rubber material. The head member includes a closed top and an open bottom and is configured to fit snuggly on a player's thumb. The anchor sheath is an open cylindrical object constructed of an interwoven mesh material. The mesh material is flexible and interlaced such that its diameter increases when opposed ends of the sheath are compressed toward one another and its diameter decreases when opposed ends are urged away from one another. Therefore, a player may extend his thumb through the sheath and into the head member when the ends of the sheath are compressed toward one another or at least fully relaxed. Removing one's thumb from the thumb sleeve also requires this compressed or relaxed condition. When the sheath is stretched completely along a player's thumb, such as during or in preparation for game play, the sheath fits tightly around the thumb to stabilize and anchor the head member.

Therefore, a general object of this invention is to provide a thumb sleeve for wear by a player during a thumb wrestling game.

Another object of this invention is to provide a thumb sleeve, as aforesaid, which includes a head member in the form of a thumb puppet.

Still another object of this invention is to provide a thumb sleeve, as aforesaid, which anchors and stabilizes the position of the head member with an interwoven anchoring mesh sheath.

Yet another object of this invention is to provide a thumb sleeve, as aforesaid, in which the head member is in a form representative of a familiar wrestling, cartoon or celebrity character.

Other objects and advantages of this invention will become apparent from the following description taken in connection with the accompanying drawings, wherein is set forth by way of illustration and example, embodiments of this invention.

BRIEF DESCRIPTION OF THE DRAWINGS

FIG. 2b is front view of the thumb sleeve as in FIG. 2a; and

DESCRIPTION OF THE PREFERRED EMBODIMENT

Figure 1:
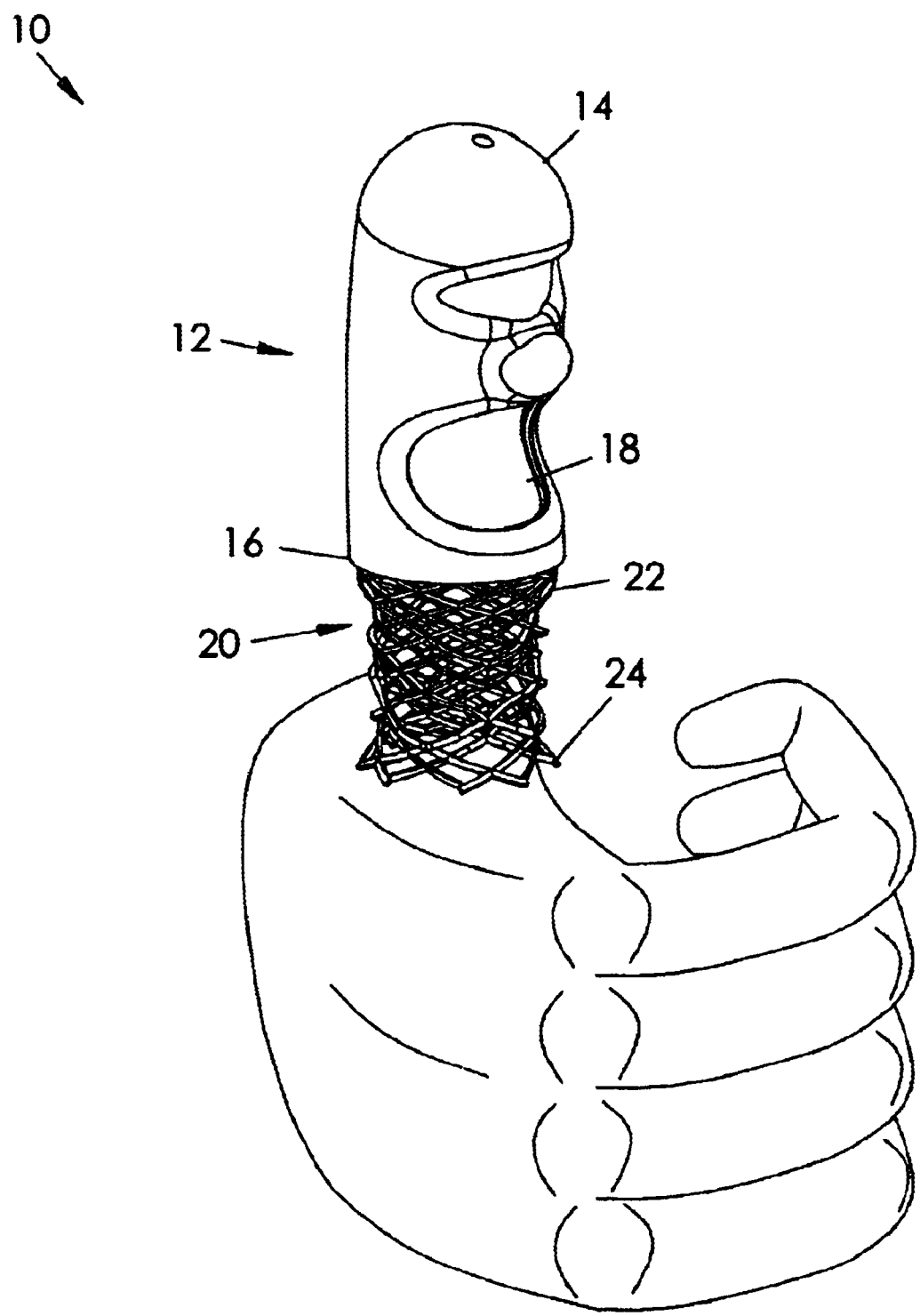
FIG. 1 is a perspective view of a thumb sleeve according to a one embodiment of the invention being worn upon the thumb of a player.
Figure 2A:
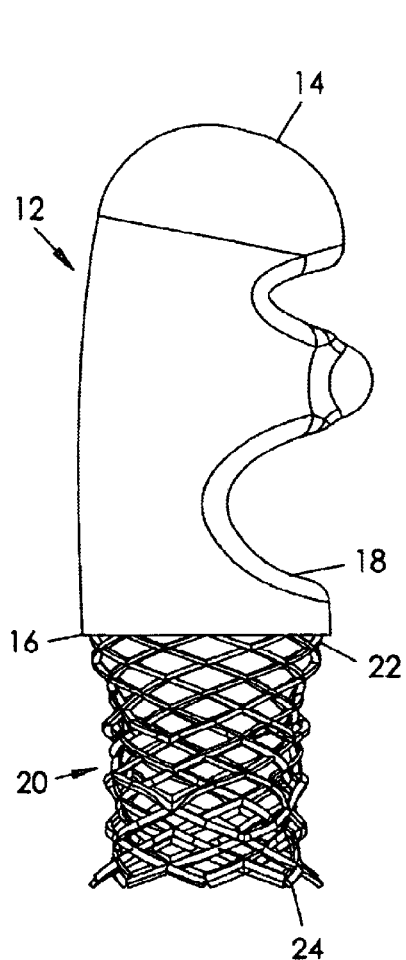
FIG. 2a is a side view of the thumb sleeve as in FIG. 1 removed from a player's thumb.
Figure 2B:
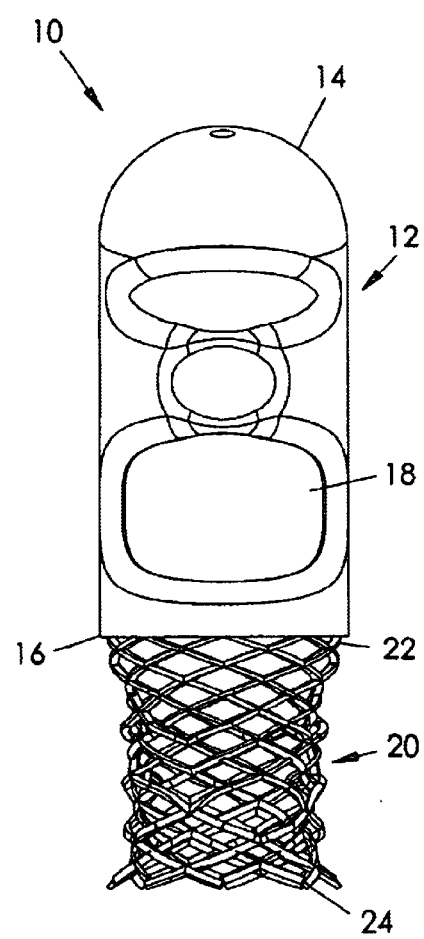

A thumb sleeve according to the present invention will now be described with reference to FIGS. 1 through 3 of the accompanying drawings. A thumb sleeve 10 according to one embodiment of the present invention includes a head member 12 connected to an anchoring sheath 20 (FIGS. 1–2b). The head member 12 is preferably constructed of a resilient material such as urethane rubber and includes a hollow generally cylindrical configuration having a closed upper end 14 and defining an open lower end 16.

The head member 12 defines at least one opening 18 between the upper and lower ends although two opening are preferable so as to be representative of a wrestler, cartoon, or celebrity character. Indicia (not shown) may also be imprinted on the head member 12 to enhance recognition of the head member 12. The configuration and construction of the head member 12 are such that the head member 12 is adapted to fit snuggly on a distal segment of a player's thumb relative to a player's hand, i.e. on the thumb segment between the outer tip of the thumb and the intermediate thumb knuckle (FIG. 1).

The anchoring sheath 20 includes an open cylindrical configuration of interwoven mesh material having a first end 22 connected to the lower open end 16 of the head member 12 and includes a second free end 24. The interwoven mesh material is flexible and preferably constructed of a plurality of interlaced rush stems of the type used in baskets and the like. The anchoring sheath 20 is intended to surround the proximal segment of a thumb relative to a player's hand, i.e. the thumb portion between the hand and the intermediate thumb knuckle (FIG. 1).

The interwoven configuration defines an interior diameter that increases or decreases depending on whether the ends of the sheath are compressed or extended. More particularly, the diameter of the sheath 20 increases when the first 22 and second 24 ends thereof are urged toward one another, i.e. compressed or relaxed. Conversely, the diameter of the sheath 20 decreases when the first 22 and second 24 ends thereof are urged away from one another, i.e. the sheath is stretched. Therefore, when a player inserts his thumb into the head member 12 and stretches the anchoring sheath 20 toward his hand, the diameter of the sheath 20 contracts for a tight, secure fit. Conversely, when the ends of the anchoring sheath 20 are urged toward one another, the diameter of the sheath 20 is expanded and the player's thumb may be slidably removed therefrom, such as when game play has ceased.

In use, a thumb sleeve 10 according to the present invention may be worn by each of two players. A thumb may be inserted into the anchoring sheath 20 and into the head member 12 using the technique described above. When the thumb sleeve 10 is stretched along a player's thumb, it will remain stationary even during vigorous game play. When play is complete, the thumb sleeve 10 may be easily removed by urging the ends of the sheath toward one another.

Figure 3:
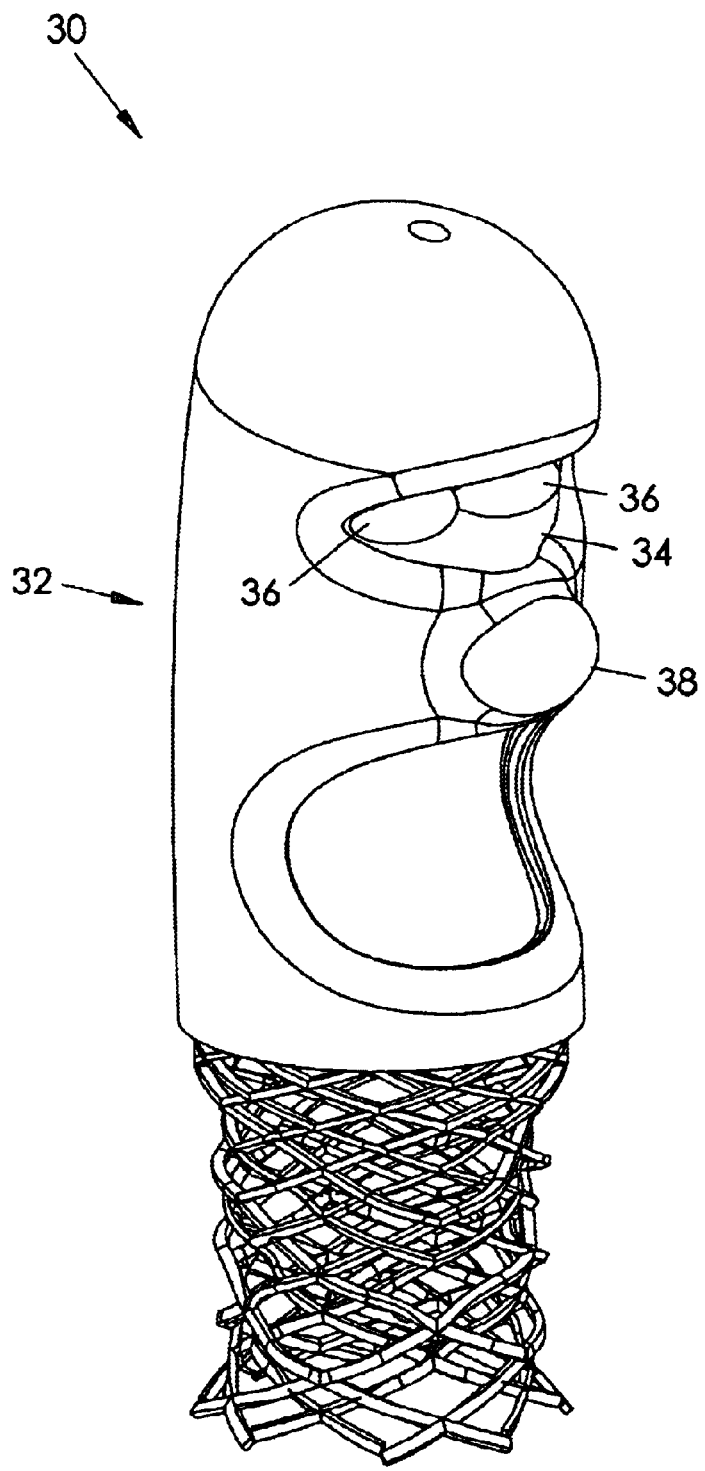
FIG. 3 is a perspective view of a thumb sleeve according to another embodiment of the present invention.

Another embodiment of a thumb sleeve 30 is shown in FIG. 3 and includes a construction that is substantially similar to the thumb sleeve 10 previously described except as specifically noted below. The thumb sleeve 30 according to this embodiment includes a pair of light emitting diodes (LED's) 36 positioned interiorly adjacent an upper opening 34 of the head member 32. When energized, these LED's 36 are representative of eyes. A battery is also included and may be positioned interiorly adjacent the head member nose 38. The nose 38 may also be configured as a battery compartment. The battery and LED's 36 are electrically connected with wires in a conventional manner.

It is understood that while certain forms of this invention have been illustrated and described, it is not limited thereto except insofar as such limitations are included in the following claims and allowable functional equivalents thereof.

Having thus described the invention, what is claimed as new and desired to be secured by Letters Patent is as follows:

1. A thumb sleeve for use in playing a thumb wrestling game, comprising:
   a head member adapted to fit snuggly on a thumb of a player; and
   a sheath constructed of interwoven mesh material having a first end connected to said head member and a second free end, said sheath defining a diameter adapted to increase when said first end is urged toward said second free end and to decrease when said first end is urged away from said second free end;
   wherein said head member includes a generally cylindrical configuration having a closed upper end and defining an open lower end connected to said first end of said sheath, said closed upper end adapted to fit snuggly about the tie of a player's thumb; and
   wherein said head member is constructed of a rubber material.

2. The thumb sleeve as in claim 1 wherein said head member includes indicia and defines at least one opening between said upper and lower ends indicative of a wrestling character.

3. The thumb sleeve as in claim 1 wherein said head member is constructed of a rubber material.

4. The thumb sleeve as in claim 1 further comprising:
   a battery positioned within said head member; and
   a light emitting diode attached to an outer surface of said head member and electrically connected to said battery for being selectably energized.

5. The thumb sleeve as in claim 1 wherein said head member includes indicia indicative of a cartoon character.

6. The thumb sleeve as in claim 1 wherein said sheath includes a generally cylindrical configuration constructed of a flexible material.

7. The thumb sleeve as in claim 1 wherein said interwoven mesh material of said sheath includes a plurality of woven rush stems.

8. A thumb sleeve for use in playing a thumb wrestling game, comprising:
   a head member having a generally cylindrical configuration adapted to fit snuggly on a thumb of a player, said head member having a closed upper end and an open lower end;
   an anchoring sheath having an open cylindrical configuration with a first end connected to said lower end of said head member and a second free end for receiving said player's thumb therethrough, said anchoring sheath constructed of interwoven mesh material and defining a diameter adapted to increase when said first end is urged toward said second free end and to decrease when said first end is urged in a direction opposite said second free end; and
   wherein said head member includes indicia and defines at least one opening between said upper and lower ends of said bead member indicative of a wrestling character.

9. The thumb sleeve as in claim 8 wherein said head member includes indicia indicative of a cartoon character.

10. The thumb sleeve as in claim 8 wherein said bead member is constructed of a resilient rubber material.

11. The thumb sleeve as in claim 8 wherein said interwoven mesh material includes a plurality of interlaced strands of rush stems.

12. The thumb sleeve as in claim 8 further comprising:
   a battery attached to an inner surface of said head member; and
   at least one light source attached to said head member and electrically connected to said battery for being selectively energized.

* * * * *